United States Patent [19]

Wada et al.

[11] Patent Number: 4,602,640

[45] Date of Patent: Jul. 29, 1986

[54] BIOMEDICAL ELECTRODE

[75] Inventors: Shintaro Wada; Hisanori Takahashi; Yoichi Nomura, all of Osaka, Japan

[73] Assignee: Nitto Electric Industrial Co., Ltd., Osaka, Japan

[21] Appl. No.: 761,282

[22] Filed: Aug. 1, 1985

[30] Foreign Application Priority Data

Oct. 1, 1984 [JP] Japan .................................. 59-206719

[51] Int. Cl.$^4$ ............................................... A61B 5/04
[52] U.S. Cl. ..................................... 128/639; 128/640; 128/641; 128/643; 128/644; 128/803
[58] Field of Search ............... 128/639, 640, 641, 643, 128/644, 803

[56] References Cited

U.S. PATENT DOCUMENTS 4,293,636 10/1981 Okuya ................................. 430/281
4,524,087 6/1985 Engel .............................. 128/639 X Primary Examiner—Lucille M. Phynes
Attorney, Agent, or Firm—Sughrue, Mion, Zinn, Macpeak & Seas

[57] ABSTRACT

A biomedical electrode comprising an electrode plate and an electroconductive material prepared by polymerizing unsaturated monomer containing a phosphoric or phosphorous group.

13 Claims, No Drawings

BIOMEDICAL ELECTRODE

FIELD OF THE INVENTION

The present invention relates to a biomedical electrode which can be attached to the skin surface of a living body for picking up accurate electrical signals from the living body.

The term "biomedical electrode" as used hereinafter means an electrode for establishing an electrical connection between the skin of a living body and an electromedical apparatus.

BACKGROUND OF THE INVENTION

While many biomedical electrodes are known in the art, they use water-containing electroconductive materials such as conductive creams, pastes, and gels that incorporate natural polymers such as karaya gum so as to provide good contact between the skin surface and the electrode and reduce electrical resistance across the skin-electrode interface. Such conductive materials are placed between the skin and the electrode plate so as to ensure good electrical connection of the skin surface to biomedical diagnostic equipment such as high-impedance electro-myographs and electrocardiographs. Conductive creams and pastes are unpleasant to use, are sloppy and will often foul the skin surface.

U.S. Pat. No. 4,125,110 teaches the use of natural polymers as conductive materials, but since they contain water as the major ingredient, provision must be made for preventing loss of water such as by evaporation in order to maintain the desired stable electrical characteristics prior to use. Water evaporation also occurs during use of the electrode and the flexibility of the gel, which contains natural polymers as the basic component, is reduced to such an extent that strong adhesion to the skin surface is not ensured. Because natural polymers originate in nature, there is a great inconsistency in the physical and chemical properties of natural polymers and in the amount of impurities present. Furthermore, the natural polymers which usually contain water support growth of microorganisms and have the potential for creating adverse skin sensitivities including antigen-antibody reactions and allergic reactions.

As a common problem associated with these conductive creams, pastes and natural polymer gels, they contain water as a conductive ingredient and require elaborate packaging to prevent loss of water prior to use. As the water content decreases, the electrical properties of the electrode are impaired, making them unsuitable for prolonged use on the skin which will dry out with time.

In order to overcome many problems associated with these "wet type" electrodes, biomedical electrodes have been proposed that utilize adhesives impregnated with conductive particles (e.g., metal particles) instead of water as the conductive material. These "dry type" electrodes have improved adhesion to the skin surface, can be securely attached to the skin and are free from the problems associated with the presence of water, but one great disadvantage results from the fact that such electrodes generally do not provide stable electrical signals.

It is speculated that dispersed conductive filler particles in the adhesive form a discontinuous, electrically conductive path which develops non-uniform electrical fields between particles, causing high signal/noise (S/N) ratios which are detrimental to the functions of biomedical electrodes.

Biomedical electrodes have also been proposed, which use, in place of the conductive natural polymers described above, polymers including monomeric units of carboxylic acid or salts thereof, or nonionic hydrophilic polymers including water-soluble monomeric units as disclosed in, for example, U.S. Pat. Nos. 4,066,078, 4,352,359 and 4,273,135, and such biomedical electrodes have proved to some extent satisfactory.

SUMMARY OF THE INVENTION

As a result of various studies to overcome the problems of the conventional electrodes, it has been found that materials produced by polymerizing unsaturated monomers having a specific functional group, namely a phosphoric or phosphorous group, have good electroconductivity and exhibit low impedance when they are applied to the skin of the living body.

Accordingly, an object of the present invention is to provide a biomedical electrode which is free from the problems involved in the conventional biomedical electrodes and can be securely attached to the skin surface a living body without fouling it, is capable of picking up accurate and stable electrical signals, and is simple to use.

The biomedical electrode according to the present invention comprises an electrode plate and an electrically conductive material produced by polymerizing an unsaturated monomer containing a phosphoric or phosphorous group.

In the preferred embodiment, the biomedical electrode according to the present invention contains an electrically conductive material comprising a copolymer of 3 wt % or more of a phosphoric or phosphorous group-containing unsaturated monomer and 97 wt % or less of an alkyl ester of (meth)acrylic acid, or a mixture of such a copolymer and an alcohol and/or water.

DETAILED DESCRIPTION OF THE INVENTION

The phosphoric or phosphorous group-containing unsaturated monomer used in the present invention is capable of dissociating ions and, like carboxyl group containing unsaturated monomers, dissociates hydrogen ions to become anionic. The unsaturated monomers used in the present invention have such a high dissociation constant that they dissociate hydrogen ions even in the presence of a very small amount of water. Any unsaturated monomer which contains phosphoric or phosphorous groups can be used, but from the standpoint of controllability of polymerization reaction, dissociation of hydrogen ions and adhesion to the skin surface, (meth)acrylic phosphoric or phosphorous-containing monomers having the following formula are preferred.

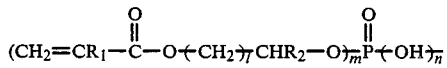

wherein $m+n=3$ provided that n is 1 or 2; $R_1$ is a hydrogen atom or a methyl group; $R_2$ is a hydrogen atom, a lower alkyl group or a halogerate lower alkyl group; l is an integer of 1 to 50.

Examples of such (meth)acrylic phosphorus-containing monomers include 2-hydroxyethylacryloyl phosphate, 2-hydroxyethylmethacryloyl phosphate, bis(2- hydroxyethylacryloyl)-phosphate, bis(2-hydroxyethylmethacryloyl)-phosphate, 3-hydroxypropylacryloyl phosphate, 3-hydroxypropylmethacryloyl phosphate, bis-(3-hydroxypropylacryloyl)-phosphate, bis-(3-hydroxypropylmethacryloyl)phosphate and 2-chloro-3-hydroxypropylmethacryloyl phosphate.

These polymers, which may be used either alone or in combination, are polymerized in the presence of organic reagents (e.g., benzoyl peroxide, azobisisobutyronitrile, ammonium persulfate and potassium persulfate) to form the intended electrically conductive material.

Electrically conductive materials which are highly tacky, provide even better adhesion and contact with the skin surface so as to ensure the picking up of stable electrical signals can be prepared by copolymerizing at least 3 wt % of the unsaturated monomer described above with up to 97 wt % of an alkyl ester of (meth)acrylic acid. In order to impart tackiness, an alkyl ester of (meth)acrylic acid wherein the alkyl group has 4 to 12 carbon atoms are preferred. Examples thereof include butyl (meth)acrylate, amyl (meth)acrylate, hexyl (meth)acrylate, octyl (meth)acrylate and dodecyl (meth)acrylate. The alkyl group in these monomers can be straight- or branched-chain and such monomers can be used either alone or in combination thereof.

The alkyl esters of (meth)acrylic acid described above can be partly replaced by copolymerizable modifier monomers. The mixture of the phosphoric or phosphorous group-containing unsaturated monomer, the alkyl ester of (meth)acrylic acid and the modifier monomer is subjected to copolymerization. Examples of such modifier monomers are functional monomers including hydroxyl group containing monomers such as 2-hydroxyethyl (meth)acrylate and 3-hydroxypropyl (meth)acrylate, amido or amino group containing monomers such as (meth)acrylamide, dimethylaminoethyl (meth)acrylate and diethylaminoethyl (meth)acrylate, nitrile group containing monomers such as (meth)acrylonitrile, monomers containing a small amount of a carboxyl group; vinyl acetate, vinyl propionate, vinylpyrrolidone, vinylpyridine, vinylimidazole, methoxyethyl (meth)acrylate, ethoxyethyl (meth)acrylate and butoxyethyl (meth)acrylate. The type of specific modifier monomer and the amount used be properly selected depending upon the need, and the use of up to 30 wt % of such modifier monomers is preferred.

For the purpose of providing biomedical electrodes having improved electrical properties and hydrophilicity, monomers having ionically functional groups or ethylene oxide units are preferably used as the modifier monomers.

The homopolymers or copolymers described above serve as the electrically conductive material for the biomedical electrode in accordance with the present invention. In order to enhance the ion dissociation which is necessary to provide a high conductivity for the biomedical electrode, the hydrophilicity of the polymers can be further improved by incorporating 5 to 40 wt % of alcohols as wetting agents. Suitable Examples of alcohols include monohydric alcohols such as methyl alcohol, ethyl alcohol, propyl alcohol and amyl alcohol; and polyhydric alcohols such as glycerin, ethylene glycol, propylene glycol, diethylene glycol and sorbitol. Preferred examples thereof are glycerin and propylene glycol which are non-volatile and have high hydrophilicity. These two alcohols can be used in admixture. A small amount of water can be added to or adsorbed on the polymers to suppress the evaporation of the alcohols or enhance the electrical conductivity as well as the wetting properties by incorporation of water.

The electrically conductive material used in the biomedical electrode in accordance with the present invention has a high degree of hydrophilicity because the material comprises a polymer of the phosphoric or phosphorous group containing-unsaturated monomer. When this conductive material is used as a skin-interfacing sheet on the electrode plate and the resulting biomedical electrode is attached to the skin, the sheet absorbs moisture from air or from the skin so as to exhibit high conductivity. In most case, there is no particular need to intentionally add water to the sheet so that it will exhibit good conductivity, and the water incidental to the electrode manufacturing process (e.g., water present in the starting materials or moisture in the atmosphere) will serve the purpose.

The conductive material in accordance with the present invention which is made of the components described above is intended for use in direct contact with the skin, so in order to enable prolonged use of the electrode on the skin, the conductive material must be dermally non-irritating without comprising its ability to adhere to the skin surface. At the same time, as soon as the conductive material absorbs water, it is desired that the phosphoric or phosphorous group becomes dissociated to render the material ionically conductive. In order to meet these requirements, it is preferred that the phosphoric or phosphorous group in the conductive material is neutralized by at least 10%, preferably at least 50%, of a cationic compound. The phosphoric or phosphorous group-containing monomer is neutralized with a cationic compound before polymerization, or alternatively, the monomer is first polymerized and then neutralized with a cationic compound. The neutralized conductive material involves a relatively small possibility of skin irritation and becomes dissociated as soon as it absorbs water.

Basic compounds preferred for use in the neutralization treatment include alkali metal hydroxide such as KOH, alkaline earth metal hydroxide, amines. Amines have the greatest ability to retain water in the conductive material. Preferred amines are alkanolamines such as ethanolamine, methyl diethanolamine, diethanolamine and triethanolamine. Triethanolamine is particularly preferred.

The biomedical electrode in accordance with the present invention is fabricated by attaching the conductive material described above onto the electrode plate. In order to enhance the shape retention of the conductive material when applied to the skin and in order to ensure the prevention of any fouling of the skin surface, the interior or surface layer of the conductive material can be reinforced with a porous material such as nonwoven fabrics to the extent that the conductivity of the material is not impaired.

The electrode plate which is placed in contact with the conductive material and which transmits electrical signals picked up from the skin surface to an external diagnostic apparatus can be in a variety of forms, such as sheets made of metals such as copper, tin, silver, nickel and aluminum, sheets of compressed carbon or graphite (including conductive metallic sheets laminated on one side with insulating reinforcing materials), plastic films laminated with thin metallic layers, and conductive sheets based on paper, woven or non-woven fabrics. The electrode plate preferably have sufficient flexibility and elasticity to move as the skin moves. For this purpose, a foil electrode is desired.

For ensuring sufficient flexibility, the overall thickness of the biomedical electrode having the construction described above is preferably not more than about 500 μm, wherein the respective thicknesses of the conductive material and electrode plate portions are 10 to 300 μm and no more than 200 μm, respectively. Of course, a greater overall thickness can be employed if the electrode can maintain the desired flexibility.

As described above, the biomedical electrode in accordance with the present invention has a high capability of ion dissociation since it uses an electroconductive material prepared by polymerizing a phosphoric or phosphorous group-containing unsaturated monomer. Because of this high ion dissociating capability, the biomedical electrode exhibits a very high degree of conductivity (i.e., low impedance) by absorbing a relatively small amount of water and picks up accurate and low-noise electrical signals from the skin surface. Additionally, the conductive material made from the phosphoric or phosphorous group-containing monomer adheres so strongly to metal surfaces that particularly good results are obtained when a metal foil is used as the electrode plate. For these reasons, the biomedical electrode in accordance with the present invention exhibits very good electrical characteristics.

The following examples are provided to further illustrate the advantages of the biomedical electrode according to the present invention but should not be construed as limiting. In the Examples, all parts are by weight.

EXAMPLE 1

100 Parts of 3-hydroxypropylmethacryloyl phosphate and 900 parts of isopropyl alcohol were thoroughly mixed and homogenized in a flask. After nitrogen purging under agitation for about 1 hour at 70° C., 0.1 part of benzoyl peroxide was added to initiate polymerization which was conducted at 82.5° C. for about 5 hours under reflux. Thereafter, 30 parts of triethanolamine was added and the reaction mixture was thoroughly agitated in order to neutralize the phosphoric group. 40 parts of glycerin was added and the mixture was stirred until a uniform solution formed. The resulting solution was coated onto a 20 μm thick nickel foil to form a conductive layer having a dry thickness of 20 μm. The web was dried at 90° C. for 2 minutes to produce a biomedical electrode in accordance with the present invention having an adhesive strength of 50 g or more (for a width of 20 mm, measured according to JIS C-2107) and an impedance of 1 kΩ or less (30 mm by square, 5 V, 10 Hz AC).

EXAMPLE 2

6 Parts of 2-hydroxyethylmethacryloyl phosphate, 100 parts of n-butyl acrylate, 150 parts of distilled water and 5 parts of sodium lauryl sulfate were thoroughly mixed in a flask while conducting nitrogen purging under agitation at 65° C. for about 1 hour. Thereafter, 0.01 part of ammonium persulfate was added to initiate emulsion polymerization. About 3 hours later, the generation of the heat of reaction was substantially completed. The temperature of the flask was increased to 80° C. and aging was conducted for about 2 hours.

15 Parts of triethanolamine was added to the resulting polymer solution and the mixture was thoroughly agitated to neutralize the phosphoric group. 10 Parts of glycerin was added to make a uniform solution, which was then coated onto a 40 μm thick tin foil to form a conductive layer having a dry thickness of 40 μm. The web was dried at 100° C. for 5 minutes to produce a biomedical electrode in accordance with the present invention having an adhesive strength of 200 g or more (for a width of 20 mm, measured according to JIS C-2107) and an impedance of 1.5 kΩ (30 mm by square, 5 V, 100 Hz, AC).

EXAMPLE 3

10 Parts of 2-hydroxyethylmethacryloyl phosphate, 100 parts of 2-ethylhexyl acrylate, 2 parts of acrylic acid, 100 parts of distilled water and 5 parts of sodium lauryl sulfate were thoroughly mixed in a flask while conducting nitrogen purging under agitation at 70° C. for about 1 hour. Thereafter, 0.02 part of potassium persulfate was added to initiate emulsion polymerization. About 4 hours later, the generation of the heat of reaction was substantially completed. The temperature of the flask was increased to 80° C. and aging was conducted for about 2 hours.

10 Parts of potassium hydroxide was added to the resulting solution and the mixture was thoroughly agitated in order to neutralize the phosphoric group. 5 Parts of propylene glycol was added to make a uniform solution, which was then coated onto a 30 μm thick nickel foil to form a conductive layer having a dry thickness of 35 μm. The web was dried at 90° C. for 10 minutes to produce a biomedical electrode in accorance with the present invention having an adhesive strength of 200 g or more (for a width of 20 mm, measured according to JIS C-2107) and an impedance of 0.9 kΩ (30 mm by square, 5 V, 10 Hz AC).

While the invention has been described in detail and with reference to specific embodiments thereof, it will be apparent to one skilled in the art that various changes and modifications can be made therein without departing from the spirit and scope thereof.

What is claimed is:

1. A biomedical electrode comprising an electrode plate and an electroconductive material prepared by polymerizing unsaturated monomer containing a phosphoric or phosphorous group.

2. A biomedical electrode as in claim 1, wherein said electroconductive material is a copolymer of at least 3 wt % of the phosphoric or phosphorous group-containing unsaturated monomer and up to 97 wt % of an alkyl ester of (meth)acrylic acid.

3. A biomedical electrode as in claim 2, wherein said alkyl ester of (meth)acrylic acid has an alkyl group of 4 to 12 carbon atoms.

4. A biomedical electrode as in claim 1, wherein said electroconductive material is a mixture of the copolymer of at least 3 wt % of the phosphoric or phosphorous group-containing unsaturated monomer and up to 97 wt % of the alkyl ester of (meth)acrylic acid, and an alcohol and/or water.

5. A biomedical electrode as in claim 1, wherein said phosphoric or phosphorous group-containing unsaturated monomer is phosphoric or phosphorous group-containing (meth)acrylic monomers.

6. A biomedical electrode as in claim 1, wherein said phosphoric or phosphorous group-containing unsaturated monomers is neutralized with a basic compound.

7. A biomedical electrode as in claim 6, wherein said basic compound is one or more than two member selected from the group consisting of alkali metal hydroxide, alkaline earth metal hydroxide, amines.

8. A biomedical electrode as in claim 7, wherein said amine is an alkanolamine.

9. A biomedical electrode as in claim 8, wherein said alkanolamine is triethanolamine.

10. A biomedical electrode as in claim 2, wherein said copolymer is neutralized with a basic compound.

11. A biomedical electrode as in claim 10, wherein said basic compound is one or more than two member selected from the group consisting of alkali metal hydroxide, alkaline earth metal hydroxide, amines.

12. A biomedical electrode as in claim 11, wherein said amine is an alkanolamine.

13. A biomedical electrode as in claim 12, wherein said alkanolamine is triethanolamine.

* * * * *